United States Patent [19]

Cross et al.

[11] Patent Number: 5,267,990

[45] Date of Patent: Dec. 7, 1993

[54] MALE URINE COLLECTION DEVICES

[75] Inventors: David E. Cross, Rustington; Kenneth J. Brooks, Lancing, both of England

[73] Assignee: Smiths Industries Public Limited Company, London, United Kingdom

[21] Appl. No.: 859,974

[22] Filed: Mar. 30, 1992

[30] Foreign Application Priority Data

Apr. 17, 1991 [GB] United Kingdom ............... 9107820

[51] Int. Cl.$^5$ .................. A61F 5/458; A61F 5/453
[52] U.S. Cl. .................................. 604/352; 604/349
[58] Field of Search ............. 604/347, 349-352; 128/844; 206/69

[56] References Cited

U.S. PATENT DOCUMENTS

| | | |
|---|---|---|
| 4,416,275 | 11/1983 | Omley . |
| 4,540,409 | 9/1985 | Nystrom et al. ............ 604/349 |
| 4,784,655 | 11/1988 | Campion et al. ............ 604/349 |
| 4,863,449 | 9/1989 | Therriault et al. ........... 604/352 |
| 4,885,049 | 12/1989 | Johannesson ............ 604/349 X |
| 4,963,137 | 10/1990 | Heyden ..................... 604/349 |

FOREIGN PATENT DOCUMENTS

| | | |
|---|---|---|
| 0260025 | 3/1988 | European Pat. Off. ........ 604/349 |
| 0663151 | 11/1987 | Switzerland ................ 128/844 |
| 663151 | 11/1987 | Switzerland . |
| 2106784 | 4/1983 | United Kingdom . |
| 2120102 | 11/1983 | United Kingdom . |
| 2229922 | 10/1990 | United Kingdom ........... 604/347 |

*Primary Examiner*—Randall L. Green
*Assistant Examiner*—David H. Willse
*Attorney, Agent, or Firm*—Pollock, Vande Sande and Priddy

[57] ABSTRACT

A male urine collection device has a short sheath the rear end of which fits over the glans and a short part of the shaft of the penis. The device is of latex rubber and is between 0.6 mm and 1.0 mm thick at its rear end. At its forward end, the device has a outlet tube which is joined to the rear end by a bulbous surge chamber. The rear end of the sheath is everted back over the outlet tube at the mouth of the surge chamber and is self supporting so that, when it is held against the tip of the penis, the rear end can be pushed rearwardly to cause it to revert about the penis. An adhesive band around the rear end of the sheath is protected by a release sheet which can be removed as the sheath reverts about the penis.

9 Claims, 1 Drawing Sheet

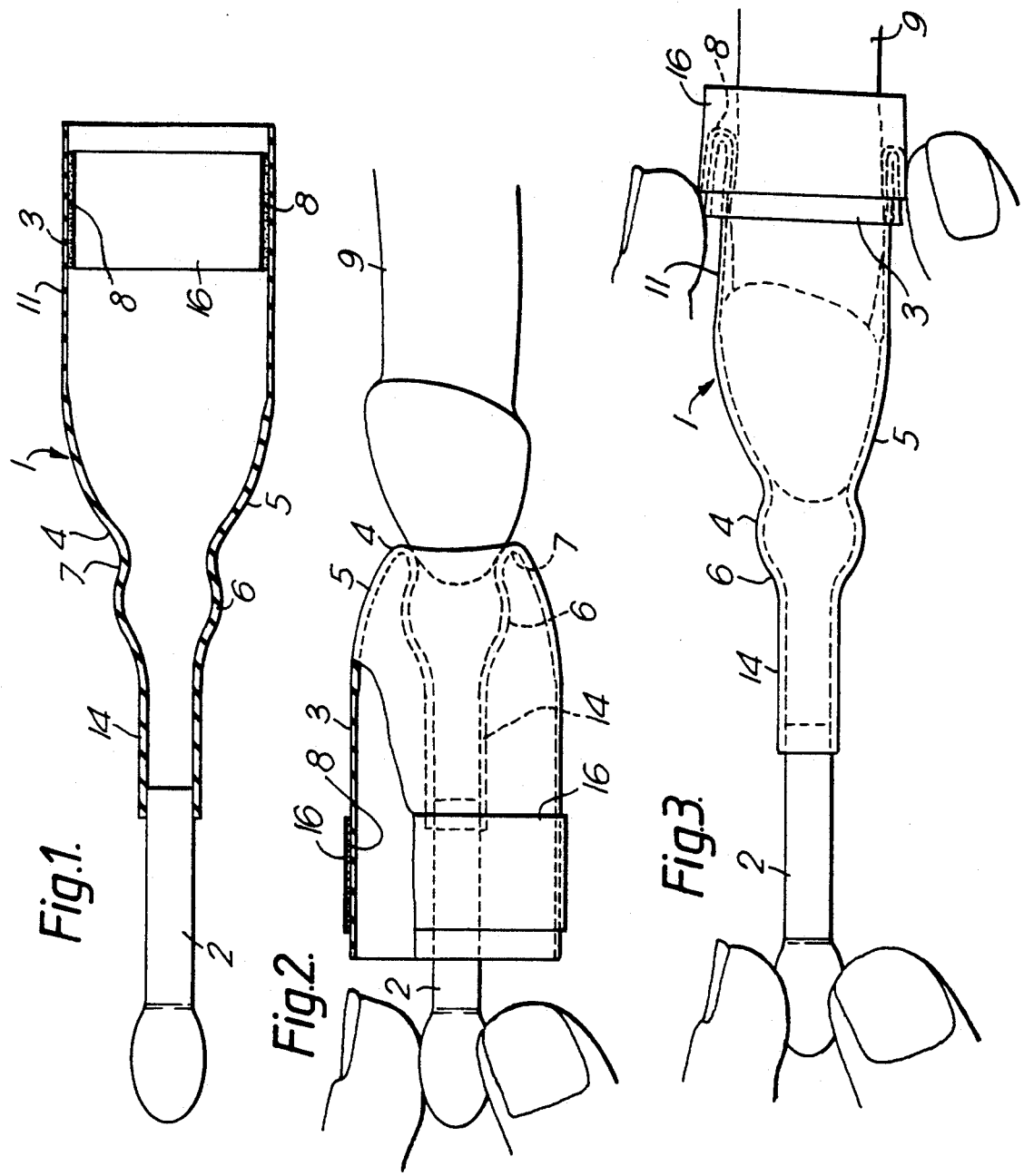

MALE URINE COLLECTION DEVICES

BACKGROUND OF THE INVENTION

This invention relates to male urine collection devices.

The invention is more particularly concerned with male urine collection devices of the type utilizing a sheath placed over the penis and connected to a urine receptacle by means of a tube.

Sheath type urine collection devices are well known in the prior art; however, the devices presently available show certain deficiencies and disadvantages.

Devices of this type are usually for use by the elderly and infirm who may have difficulty in applying such devices because of unsteady, weak or arthritic hands. It is, however, preferable that the device can be readily applied by the patient himself to avoid embarrassment.

With devices of the type described in GB 2,120,102B, which have a relatively thin-walled sheath, an applicator device is required, which makes the device more bulky and difficult to store and pack. Furthermore, such devices can be difficult to use by the infirm.

Where it is impossible for the patient to apply the device himself, it is desirable for it to be applied quickly and simply to reduce any embarrassment to a minimum.

An alternative device, as shown in GB 2106784, has a sheath rolled outwardly upon itself, with adhesive on the inner surface trapped between successive rolls of the sheath. In order to prevent successive rolls of the sheath from adhering to one another, the outer surface is laminated with a release material. The laminated construction of the sheath can increase the cost of the collection device. Such devices can also be difficult to apply to the flaccid penis and have the further disadvantage that it is necessary to contact the adhesive with the fingers when unrolling. This can lead to a reduction in adhesion if the user's fingers are not thoroughly clean.

SUMMARY OF THE INVENTION

It is an object of the present invention to provide an improved form of male urine collection device which can be readily applied by the patient and can be manufactured at low cost.

According to one aspect of the present invention there is provided a male urine collection device comprising a sheath adapted to be fitted about the glans and a part at least of the shaft of the penis, the sheath having an outlet tube at its forward end and an open rear end which is everted back over the forward end of the sheath, the device including a region of adhesive on the outer surface of the everted sheath which is protected before application by a removable release sheet, and the thickness and material of the sheath being such that in its everted state the sheath is self supporting and can be pushed axially in a rearward direction so that it reverts about the penis.

The sheath preferably has a bulbous surge chamber at the rear end of the outlet tube and the sheath is preferably everted about the rear end of the surge chamber. The sheath may be of latex rubber, the thickness of which in the region of the rear end is between 0.6 mm and 1.0 mm and in the region of the outlet tube is substantially 1.2 mm.

The device may include a rod shape applicator removably secured to the outlet tube which can be gripped to facilitate application of the collection device.

According to a second aspect of the present invention there is provided a method of applying a male urine collection device, comprising the steps of: providing a collection device having a sheath with an outlet tube at its forward end and a rear end that is everted back over the forward end and is self-supporting, the device having a region of adhesive on the outer surface of the everted sheath and a release sheet protecting the adhesive that is removed before contact of the adhesive with the skin; placing the device against the tip of the penis; and gripping the everted rear end of the sheath and pushing it axially rearwardly so that the sheath reverts about the shaft of the penis.

The release sheet may be removed after placing the device against the tip of the penis by allowing the release sheet to peel away from the sheath as the adhesive region is reverted about the shaft of the penis.

A male urine collection device and a method for applying such a device in accordance with the present invention, will now be described, by way of example, with reference to the accompanying drawings.

BRIEF DESCRIPTION OF THE DRAWINGS

FIG. 1 is a sectional view of the urine collection device with an applicator rod;

FIG. 2 is a side elevation of the urine collection device at the commencement of the application procedure; and FIG. 3 is a side elevation of the urine collection device during the application procedure.

DESCRIPTION OF THE PREFERRED EMBODIMENTS

With reference to FIG. 1, the collection device 1 comprises a cylindrical sheath 11 suitable to be fitted around the glans and shaft of a penis.

The sheath 11 is made by dipping from latex rubber and comprises a rear portion 3, an intermediate portion 4 and an outlet tube 14 at the forward end. The rear portion 3 is relatively short compared with previous devices, being about 45 mm long and having a constant diameter along its length of about 33 mm; the wall thickness of the rear portion is also relatively thick compared with previous devices, being between about 0.6 mm and 1.0 mm. The intermediate portion 4 comprises a funnel portion 5 and a bulbous surge chamber 6. The funnel portion 5 tapers in diameter from the rear portion 3 to a waist 7 of diameter about 14 mm. The waist 7 forms the mouth of the rear of the surge chamber 6 which has a diameter at its widest point of about 16 mm. The overall length of the intermediate portion 4 is about 45 mm. The thickness of material in the intermediate portion 4 and the outlet tube 14 is greater than that in the rear portion, being about 1.2 mm.

Around the inside of the sheath 11, close to the rear end of the rear portion 3, there is an annular band 8 of pressure-sensitive adhesive which is about 20 mm wide. The adhesive 8 is of a conventional kind which is not irritating to the skin and is moisture resistant, being sufficiently strong to maintain the sheath in position while enabling it to be removed without pain.

The collection device 1 also includes a solid, cylindrical applicator rod 2 which is a push fit in the forward end of the outlet tube 14. The rod 2 is made of a relatively rigid plastics material, and is about 60 mm long with a diameter of about 9 mm. The applicator rod 2 is used to apply the sheath 11 to the penis 9 in a manner that is described in detail below.

The collection device is supplied to the patient in the configuration shown in FIG. 2, which is ready for application. The rear portion 3 and the funnel portion 5 are folded inside out about the waist 7 so that they are everted and extend forwardly, coaxially outside the surge chamber 6 and outlet tube 14. In this configuration, the free end of the rear portion 3 not extends forwardly beyond the forward end of the outlet tube 14. The adhesive 8 is presented externally on the outer surface of the everted sheath 11 and is protected by a release sheet 16, such as a strip of siliconized paper.

The thickness, size and material of the sheath 11 are such that, in the everted configuration, the device is self supporting, that is, it is sufficiently rigid to maintain a generally circular shape without the need for any additional member to support the sheath. This contrasts with previous devices made of thinner material which are more flexible and which have to be supported by a separate, rigid sleeve internally of the everted portion.

To apply the device, the user grips the free end of the applicator rod 2 between the finger and thumb of his left hand and holds the rear of the device (now provided by the mouth of the surge chamber 6) up to the tip of the penis 9, as shown in FIG. 2. The user now lightly grips the rear portion 3 close to its forward end (that is, close to funnel portion 5) with the finger and thumb of his other hand and pushes this rearwardly so that the funnel portion flips over about the glans of the penis 9, to the position shown in FIG. 3. The user then moves his grip further back along the rear portion 3, so that it is held in the region of the adhesive release sheet 16. He continues to push the rear portion 3 rearwardly until the adhesive region 8 starts to revert about the shaft of the penis 9. When this happens, the release sheet 16 peels away from the rear portion 3 because it maintains a tubular configuration. Further movement rearwardly causes more of the adhesive region 8 to contact the skin of the penis while the forward edge of the release sheet 16 moves closer to the base of the penis, in advance of the folded edge of the sheath itself. This has the advantage that the release sheet 16 pushes pubic hair away from the rear of the sheath 11 and reduces the risk o it being stuck to the adhesive 8 or trapped under the sheath. In this way, discomfort to the user is reduced.

The sheath is then gently squeezed in the region of the adhesive band 8 to ensure firm adhesion and an effective seal.

The release sheet 16 could alternatively be removed manually by peeling away from the sheath at any time before the adhesive region 8 is reverted about the penis.

The material of the rear portion 3 is sufficiently rigid to enable it to be pushed axially, in contrast with previous, thinner devices which would buckle if pushed axially.

After reverting the sheath 11, the applicator rod 2 is removed by gripping the surge chamber 6 with one hand and pulling the rod out of the outlet tube 14, using the other hand. The outlet tube 14 is then connected to a urine drainage tube (not shown) in the usual way.

The device of the present invention has several advantages. It is easy to apply, especially by men with limited dexterity. The increased thickness of the device makes it relatively robust and less likely to damage or tearing. Furthermore, the device can be packed relatively flat because it does not require the use of a supporting applicator sleeve.

The applicator rod need not be solid but could be of tubular shape, with a through bore, and could be arranged to form a coupling with the urine drainage tube. An applicator rod is not essential since it is possible to grip the outlet tube 14 directly by pushing the finger and thumb within the open end of the everted sheath. The outlet tube could be lengthened to facilitate this, although it is generally preferable to keep the tube short so as to reduce the risk of kinking.

What I claim:

1. In a male urine collection device of the kind comprising a sheath adapted to be fitted about the glans and a part at least of the shaft of the penis, the sheath having an outlet tube at its forward end and an open rear end which is everted back over the forward end of the sheath, the improvement wherein the device includes a region of adhesive on the outer surface of the everted sheath which is protected before application by a removable release sheet, the internal diameter of the sheath being substantially equal to the diameter of the penis, and the thickness and material of the sheath alone rendering the sheath self supporting in its everted state, even without said release sheet, so that the sheath can be pushed axially in a rearward direction to cause it to revert about the penis with the entire adhesive region contacting the surface of the penis.

2. A device according to claim 1, wherein the sheath has a bulbous surge chamber at the rear end of the outlet tube.

3. A device according to claim 2, wherein the sheath is everted about the rear end of the surge chamber.

4. A device according to claim 1, wherein the sheath is of latex rubber.

5. A device according to claim 1, wherein the thickness of the sheath in the region of the rear end is between 0.6 mm and 1.0 mm.

6. A device according to claim 5, wherein the thickness of the sheath in the region of the outlet tube is substantially 1.2 mm.

7. A device according to claim 1, wherein the device includes a rod shape applicator which is removably secured to the outlet tube and which can be gripped to facilitate application of the collection device.

8. A method of applying a male urine collection device to the penis of a user, comprising the steps of: providing a collection device having a sheath with an outlet tube at its forward end and a rear end that is everted back over the forward end, the material and thickness of the sheath rendering the sheath itself self-supporting, the internal diameter of the sheath being substantially equal to the diameter of the penis, the device having a region of adhesive on the outer surface of the everted sheath and a release sheet protecting the adhesive; placing the device against the tip of the penis; gripping the everted rear end of the self supporting sheath and pushing it axially rearwardly so that the sheath reverts about the shaft of the penis and so that the entire adhesive region contacts the surface of the penis; and removing the release sheet before contact of the adhesive region with the surface of the penis.

9. A method according to claim 8, wherein the release sheet is removed after placing the device against the tip of the penis by allowing the release sheet to peel away from the sheath as the adhesive region is reverted about the shaft of the penis.

* * * * *